US012650404B2

(12) United States Patent
  Parajuli

(10) Patent No.: US 12,650,404 B2
(45) Date of Patent: Jun. 9, 2026

(54) THIOSULFATE SENSOR

(71) Applicant: Badger Meter, Inc., Milwaukee, WI (US)

(72) Inventor: Rishi Parajuli, Schwenksville, PA (US)

(73) Assignee: Badger Meter, Inc., Milwaukee, WI (US)

( * ) Notice: Subject to any disclaimer, the term of this patent is extended or adjusted under 35 U.S.C. 154(b) by 107 days.

(21) Appl. No.: 18/380,268

(22) Filed: Oct. 16, 2023

(65) Prior Publication Data
  US 2025/0123234 A1       Apr. 17, 2025

(51) Int. Cl.
  G01N 27/404 (2006.01)
  G01N 27/30 (2006.01)
  G01N 33/00 (2006.01)

(52) U.S. Cl.
  CPC .......... G01N 27/404 (2013.01); G01N 27/30 (2013.01); *G01N 33/0042* (2013.01); *G01N 33/0044* (2013.01)

(58) Field of Classification Search
  CPC .. G01N 27/404; G01N 27/30; G01N 33/0042; G01N 33/0044
  See application file for complete search history.

(56) References Cited

U.S. PATENT DOCUMENTS

| | | | |
|---|---|---|---|
| 5,770,039 A * | 6/1998 | Rigney | G01N 27/404 204/418 |
| 8,329,024 B2 * | 12/2012 | Henry | G01N 27/4168 204/402 |
| 2004/0197922 A1 * | 10/2004 | Cooper | G01N 33/18 422/68.1 |

OTHER PUBLICATIONS

Ryon et al., "Impacts on Streams From the Use of Sulfur-Basedcompounds for Dechlorinating Industrial Effluents," Water, Air, and Soil Pollution 136: 255-268, 2002 (Year: 2002).*
Kovaleva et al., "Anodic oxidation of thiosulfate ions at a carbon-based electrode with deposited Au-particles," E3S Web of Conferences 383, 04079 (2023) (Apr. 24, 2023) (Year: 2023).*

* cited by examiner

*Primary Examiner* — Alexander S Noguerola
(74) *Attorney, Agent, or Firm* — Boyle Fredrickson SC

(57) ABSTRACT
A thiosulfate sensor having an electrode assembly including a sensing electrode including electrochemically deposited metal, a counter electrode, and a reference electrode is described. The thiosulfate sensor further includes an electrolyte chamber including an electrolyte solution therein, the electrolyte chamber receiving the electrode assembly through a first opening to immerse the electrode in the electrolyte and an electrolyte chamber porous membrane covering a second opening, where the porous membrane is configured to receive a flowing fluid therethrough to allow the detection of thiosulfate in the flowing fluid.

14 Claims, 4 Drawing Sheets

THIOSULFATE SENSOR

FIELD OF THE INVENTION

This application relates to a sensor for monitoring residual thiosulfate concentration. More specifically, the present invention is direct to an electrochemical sensor for measurement of thiosulfate ion in aqueous solution including a sensing electrode having rhodium nanoparticles deposited on the conductive surface.

BACKGROUND

Both potable water and wastewater are typically chlorinated using a process of water chlorination. Water chlorination is the process of adding chlorine or chlorine compounds such as sodium hypochlorite to water. This process is used to kill bacteria, viruses, and other microbes in water. Chlorination is used to prevent the spread of waterborne diseases such as cholera, dysentery, and typhoid. However, although chlorination has a valuable purpose, it is often necessary to thereafter remove chlorine or excess chlorine from potable water and/or wastewater. Dechlorination is the process of removing residual chlorine from water prior to delivery to consumers or discharge into the environment using additional chemicals and/or other additives.

Salts of thiosulfates such as calcium thiosulfate and sodium thiosulfate are used by both potable and wastewater industries for one such dechlorination process. Such salts are also used for ozone quenching and neutralization of sodium hypobromite and ozone, in addition to chlorine, in water treatment.

Water treatment using salts of thiosulfates are known to produce residual thiosulfate ions. Residual thiosulfate is useful as an indicator that all the chlorine has been successfully removed and the dechlorination process was complete. If no thiosulfate is present, it may be that not all the chlorine was neutralized. Residual thiosulfate concentration in both potable and wastewater may also be an issue because it can be, for example, a skin tissue irritant. In another example, an excess level of residual thiosulfate concentrations in refinery applications is linked to corrosion of equipment and piping failures.

As such, thiosulfate analysis is performed in water applications to identify residual thiosulfate in water. Currently, thiosulfate analysis has been mostly executed by spectroscopic such as atomic absorption spectroscopy (AAS), chromatographic techniques such as Ion Chromatography (IC), a combination thereof such as gas chromatography-mass spectroscopy (GS-MS) or inductively coupled plasma mass spectrometry (ICP-MS), or a wet chemical method such as iodometry. These are some examples of the traditional residual thiosulfate detection tests in a laboratory environment using traditional instruments over a longer period of time. However, these techniques are not suitable for real time monitoring of thiosulfate ions in a flow environment such as is typically found in systems providing potable water and/or wastewater treatment and disposal. Yet further, thiosulfate itself is relatively unstable, such that delayed, lab transported sample may not provide accurate results.

U.S. Pat. No. 8,097,212 illustrates one type of system that can be used to detect contaminants in a fluid distribution system. The problem with this system is that it does not describe any sensor to be used in the intended application in sufficient detail to allow one of ordinary skill in the art to practice the sensor and implement residual thiosulfate detection in a constantly flowing system.

What is needed is a thiosulfate sensor configured for real-time monitoring of a fluid distribution system. What is further needed is such a device configurable for use in a water metering system.

SUMMARY OF THE INVENTION

The present invention is directed to a simple, convenient, rapid, accurate and precise measurement for real time monitoring for thiosulfate in potable water, wastewater, refinery, and agricultural applications. More specifically, measurement for real time monitoring for thiosulfate using an electrode material, electrolyte solution and applied bias as described herein.

In one embodiment of the invention, a thiosulfate sensor having an electrode assembly including a sensing electrode including electrochemically deposited metal, a counter electrode, and a reference electrode is described. The thiosulfate sensor further includes an electrolyte chamber including an electrolyte solution therein, the electrolyte chamber receiving the electrode assembly through a first opening to immerse the electrode in the electrolyte and an electrolyte chamber porous membrane covering a second opening, where the porous membrane is configured to receive a flowing fluid therethrough to allow the detection of thiosulfate in the flowing fluid.

In one more detailed aspect, the electrochemically deposited metal is at least one of rhodium, iridium oxide, gold, platinum, and glassy carbon. The deposited metal may be high surface area nanoparticles of the metal.

In another more detailed aspect, the electrolyte is at least one of potassium nitrate, sodium perchlorate and pH 8.5 Tris HCl buffer.

In another more detailed aspect, the electrolyte chamber membrane is a hydrophilic membrane with pore size ranging from 0.1 um to 0.2 um. The electrolyte chamber membrane may be at least one of polyvinylidene difluoride, poly ether sulfone, hydrophilic PTFE membrane, and PETE Polyester.

In another more detailed aspect, the sensor assembly includes an analyzer connection configured to receive an applied bias potential to the electrode assembly.

In another embodiment of the invention, a method for detecting residual thiosulfate in a flowing fluid in real time using a thiosulfate sensor is described. The method includes positioning a thiosulfate sensor in a flow cell configured to receive fluid from the flowing fluid, the thiosulfate sensor including an electrode assembly including a sensing electrode including electrochemically deposited metal, a counter electrode, and a reference electrode. The thiosulfate sensor further includes an electrolyte chamber including an electrolyte therein, the electrolyte chamber receiving the electrode assembly through a first opening to immerse the electrode in the electrolyte and an electrolyte chamber porous membrane covering a second opening, wherein the porous membrane is configured to receive a flowing fluid therethrough to allow the detection of thiosulfate in the flowing fluid. The method further includes applying a bias potential to the thiosulfate sensor in the flow cell to identify a thiosulfate concentration correlated to a measured current from the thiosulfate sensor.

Other aspects of the invention, besides those discussed above, will be apparent to those of ordinary skill in the art from the description of exemplary embodiments which follows. In the description, reference is made to the accompanying drawings, which form a part hereof, and which illustrate examples of the invention.

DETAILED DESCRIPTION OF THE INVENTION

The present application is directed to a thiosulfate sensor and method for using a thiosulfate sensor configured for use in detecting residual thiosulfate in a flowing fluid environment. As an example, the thiosulfate sensor is shown in use in utility water management system. Although shown in the utility management system, the sensor may be used in any other environment where detecting thiosulfate is an issue. Although described as being used in a flowing fluid application, the sensor may alternatively be used in other environments as well.

Figure 1:
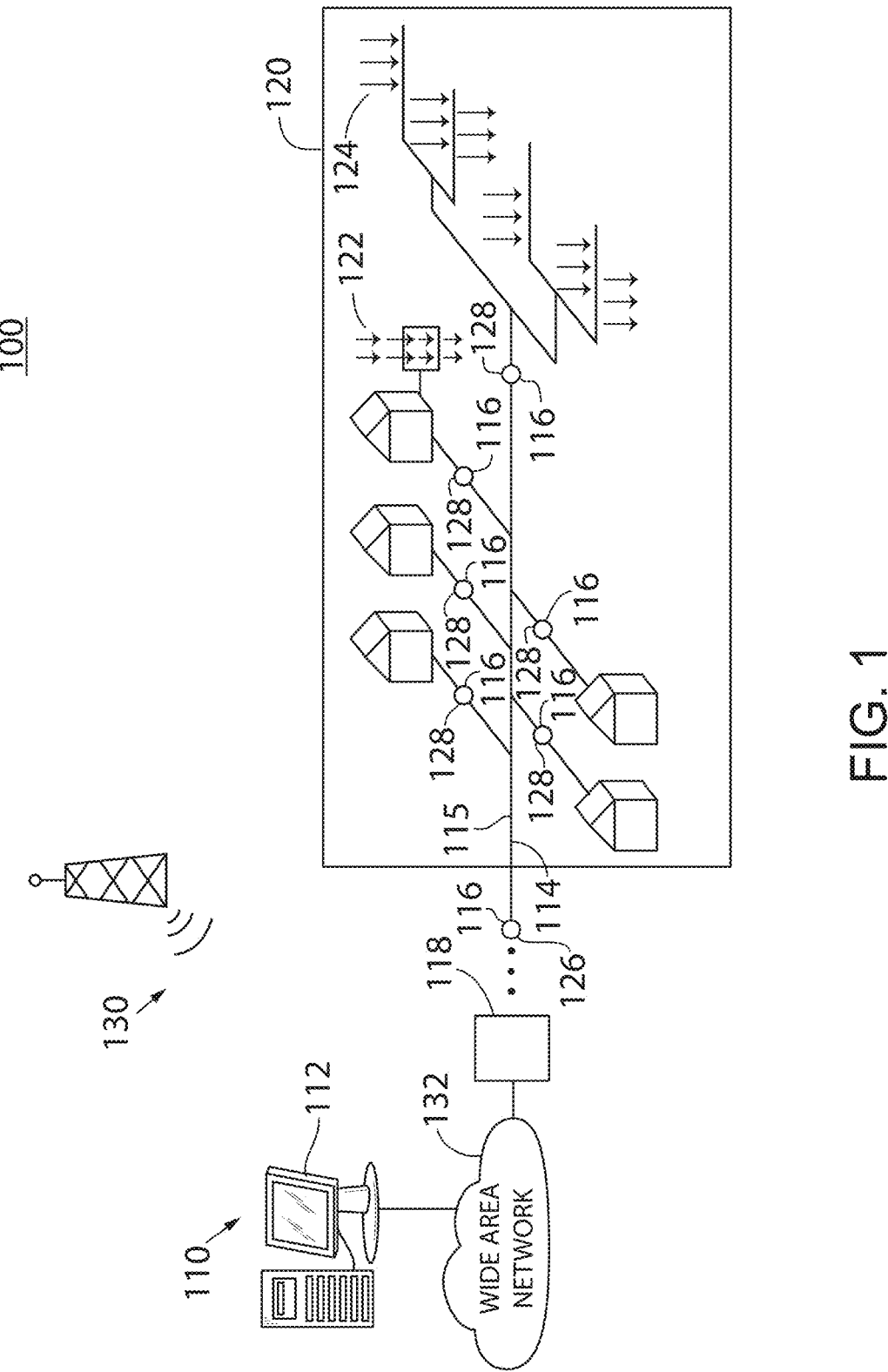
FIG. 1 is a representative diagram of a utility supply environment including a utility monitoring system, according to an exemplary embodiment.

Referring first to FIG. 1, a utility supply environment 100 is shown, according to an exemplary embodiment. Utility supply environment 100 includes a utility monitoring system 110, a utility supply usage environment 120, and a communication system 130. Utility monitoring system 110 is configured to facilitate residual thiosulfate detection in combination with utility usage information being generated by utility monitoring system 110. Environment 100 is shown according to an exemplary embodiment with an exemplary configuration, but one of ordinary skill in the art would understand that a variety of configurations and components may be used with an environment 100 to implement systems and methods described herein.

The utility monitoring system 110 includes a monitoring control system 112 and a utility supply network 114. Utility monitoring system 110 be implemented in a variety of different configurations. For example, system 110 can include additional systems or application such as a billing system, a utility supply monitoring system, a quality monitoring system, etc. that are not shown in this simplified environment but would be understood by one of ordinary skill in the art.

Monitoring control system 112 is provided for collecting flow measurement data from a network of flow measurement devices 116 in the utility supply network 114. One example of such flow measurement devices are utility meters distributed within a geographic area served by a utility are monitored by the utility. In the utility example, the control system 112 typically is connected to additional systems (not shown), such as a billing computer which requests data and imports a data file from the control system 112 to obtain meter data to produce customer statements of account for utility usage, a monitoring system for monitoring exception conditions such as contamination leakage or tampering or shut-off conditions as described in further detail below, a quality monitoring system for detecting any issues with the utility being supplied such as high thiosulfate concentration, other contamination, degradation, etc. It is also possible that, in some embodiments, the functions of these separate systems could be combined in a single system on one or more computers running multiple application programs. In this exemplary embodiment, the system is described as with reference to a water utility supply network, such as within a refinery production system, a wastewater management system, etc.

The control system 112 communicates with utility supply network 114 through communication system 130. In an exemplary communication system 130, control system 110 communicates over a wide area network (WAN) 132, such as the Internet, to a router and/or a receiver 118 receiving data in radio frequency (RF) signals from flow measurement devices 116, as described in further detail below. The receiver 118 may also be referred to as a "gateway" because it interfaces between a local area wireless network communicating with flow measurement devices 116 and wide area network 132.

Utility supply network 114 includes a network of flow measurement devices 116, each including a utility meter, a transducer, an RF (radio frequency) transmitter and a connection to a utility supply conduit 115. In this example, the devices 116 can be meter reading and transmitting units commercially offered under the Orion® trademark or the Galaxy® trademark by the assignee of the present invention. These flow measurement devices 116 transmit radio frequency (RF) signals to a receiver 118 using a local area wireless network. It should be understood that there is typically more than one receiver 118 in such a network, although only one is illustrated in FIG. 1. These devices 116 may be connected to Orion® or Galaxy® radio transmitters to transmit status data to the receiver 118.

Utility supply network 114 is shown in an abbreviated form in FIG. 1 for illustrative purposes. One of ordinary skill in the art would understand that network 114 may include hundreds or thousands of flow measurement devices 116 and miles of utility supply conduit 115. Further, the type, configuration, size, etc. of the network 114 will vary greatly depending on the utility supply needs. Additional networks may include wastewater treatment and release networks, refinery supply and disposal networks, etc.

The flow measurement devices 116 transmit data-encoded RF signals over low power RF frequencies either in the non FCC-licensed ISM (Industrial-Scientific-Medical) band from 902 MHz to 928 MHz. (Orion® AMR systems) or in the FCC-licensed frequencies such as 150-200 MHz, 325 MHz, 433.92 MHz or from 450 to 470 MHz (Galaxy® AMR systems). The flow measurement devices 116 transmit flow and other meter data to the RF receiver 118, which in this case is an Orion® receiver, that is connected through wide area network 132, in this embodiment to the Internet. In another embodiment, the receiver 118 is a gateway receiver of the type offered under the Galaxy® trademark. The control system 112 is also connected to the wide area network 132, the Internet, and can address the receivers 118 at a receiver network address which can be an Internet Protocol (IP) address of the format WWW.XXX.YYY.ZZZ—where W, X, Y and Z are values in a range from "0" to "255", such as for example: 192.168.1.175. The receiver network address can also be a uniform resource locator (URL) in the form: http://www-.google.com. As used herein, the term "meter data" should be understood to include either utility consumption data or condition status data, or both. Condition status data includes leak detection data, contaminant detection data, tamper data and shut-off valve data and other types of data concerning meter operation besides actual utility consumption data.

Figure 4:
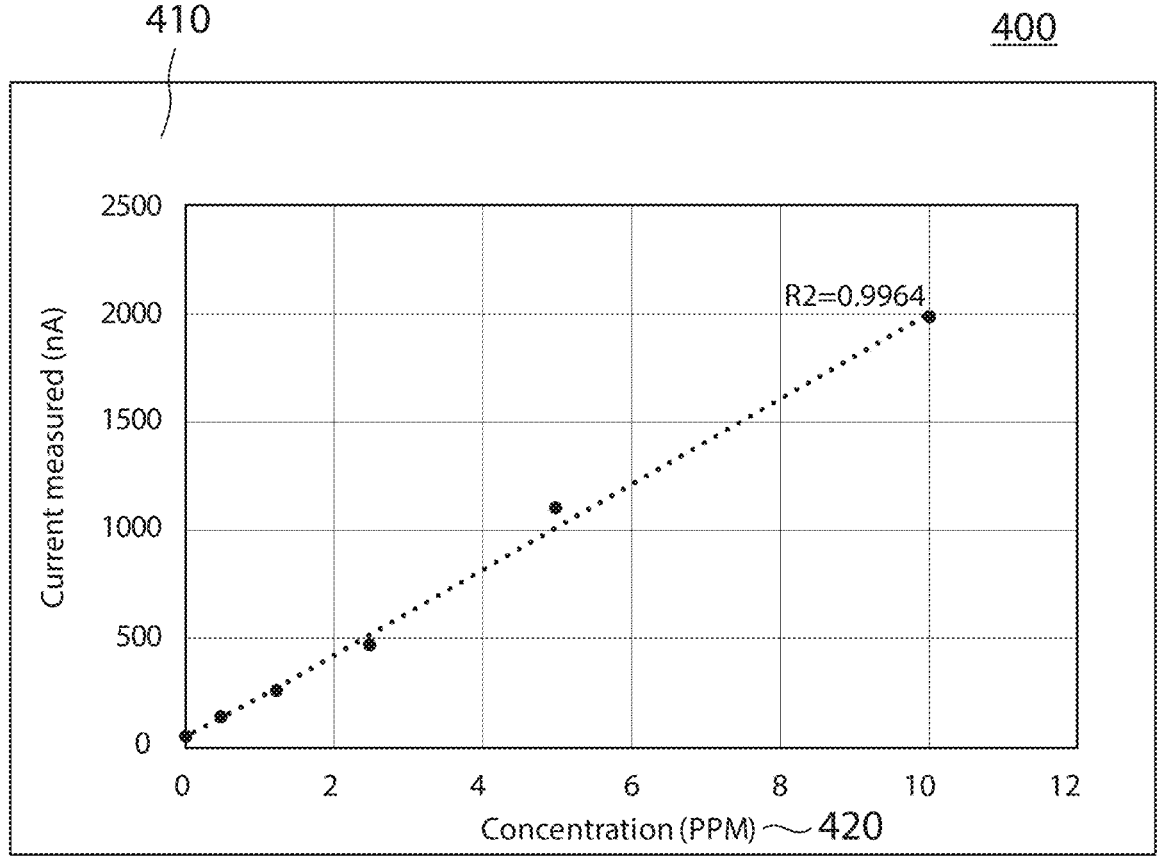
FIG. 4 is a graph illustrating thiosulfate monitoring correlating current with a measured thiosulfate, according to an exemplary embodiment.

The method and system of the present invention is implemented by control system 112 with network access to wide area network 132, which may be the Internet. The method of the invention includes communication with the receiver(s) 118 using a receiver network address that has been preset in the receiver 118 and provided to the control system 112. The control system 112 operates under the control of a stored computer program including a contaminant detection and management routine, as represented by FIG. 4. The blocks in the illustrations in FIG. 4 represent one or more program instructions in the stored computer program that are executed by a processor in the control system 112. The computer program is stored in the memory in the control system 112 but can also be stored in a tangible non-transient data storage medium or in a file for transmission on the Internet.

The invention provides a method and a system for the collection of meter data from the flow measurement devices 132 of the utility supply network and for providing improved contaminant detection and management based on allocation of the flow measurement devices 132 and contaminant sensors into utility supply network 130 as described below. The method and system can be used to facilitate contaminant location within supply network 130 such that the utility can identify water outlets that have been affected, water outlets that will be affected and water outlets that will not be affected by detected contaminants. The method and system can also be used to control the utility supply network 130, identify and facilitate contact with utility customers to flush the contaminant, etc., to respond to the contamination.

Utility supply usage environment 120 is a terrestrial environment including the utility supply network 114 including the supply conduit 114 and the flow measurement devices 116. Environment 120 may be, for example, an urban, suburban, rural, etc. area wherein water from supply network is being provided to end users for use within residences, for personal irrigation, for agricultural irrigation, etc.

Utility supply usage environment 120 includes any area of land to which water is supplied through utility supply network 114, Environment 120 can include water travelling through conduit that is metered, such as conduit 115, and conduit that is unmetered, such as any outdoor conduit and/or water usage outlet downstream from a flow measurement device 116, such a sprinkler system 122 and/or an irrigation system 124. Although sprinkler system 122 and irrigation system 124 are provided as examples, it should be understood that a variety of implementations that could include outdoor conduit and/or water usage outlets are possible.

In operation, utility supply network 114 may include one or more flow measurement devices 116, positioned upstream from the conduit 115 entering utility supply usage environment 120, designated as an inflow measurement device 126. Utility supply network 114 is configured to recognize the remainder of the flow measurement devices 116 as outflow measurement devices 128. Utility monitoring system 110 may be configured to monitor the utility supply throughout the utility supply usage environment 120. Specifically, utility monitoring system 110 may monitor the utility supply network to identify usage, quality, outages, theft, leakage, contamination, etc.

One or more devices in the utility supply usage environment 120 may be configured to include a thiosulfate sensor configured to detect residual thiosulfate in the flowing fluid environment. The sensor may be incorporated one or more flow measurement devices 116, positioned upstream from the conduit 115 entering utility supply usage environment 120, as part of a wastewater management system in an outflow measurement device 128, etc. to determine whether dechlorination has been successful, whether thiosulfate remain that may have a corrosive effect on equipment, etc.

Figure 2:
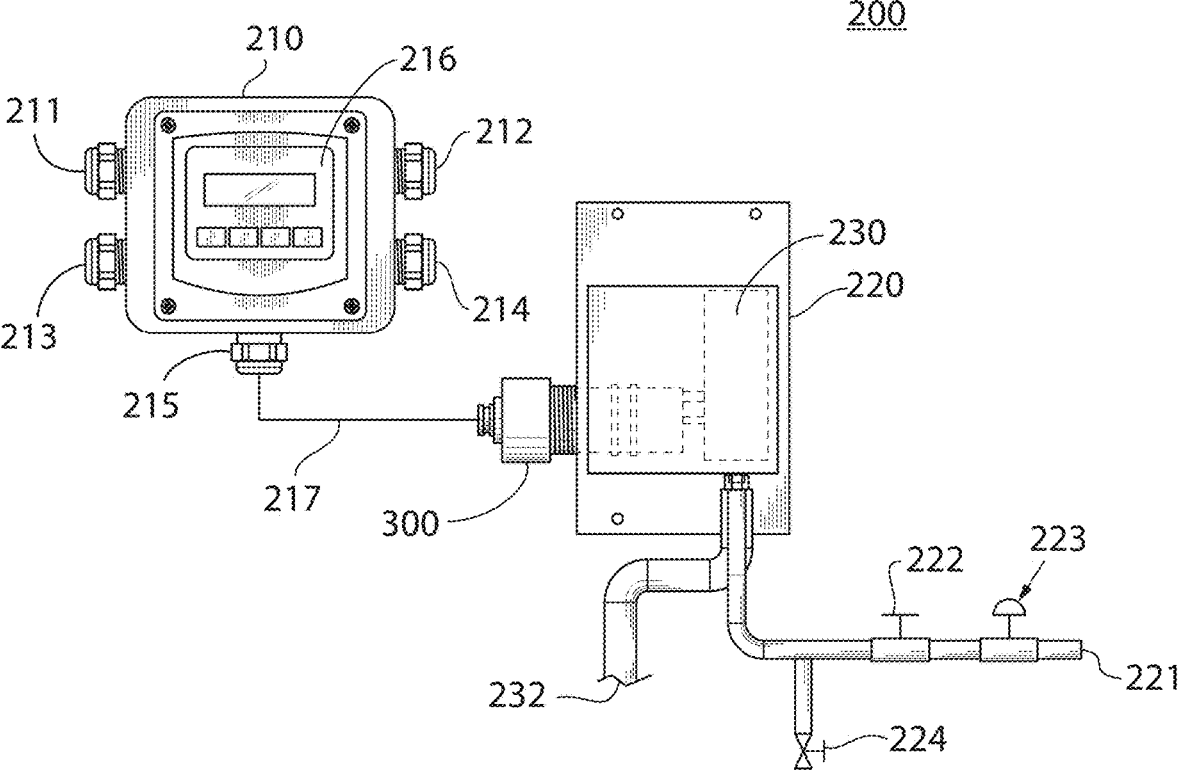
FIG. 2 is a monitoring system configured to include a thiosulfate sensor, according to an exemplary embodiment.
Figure 3:
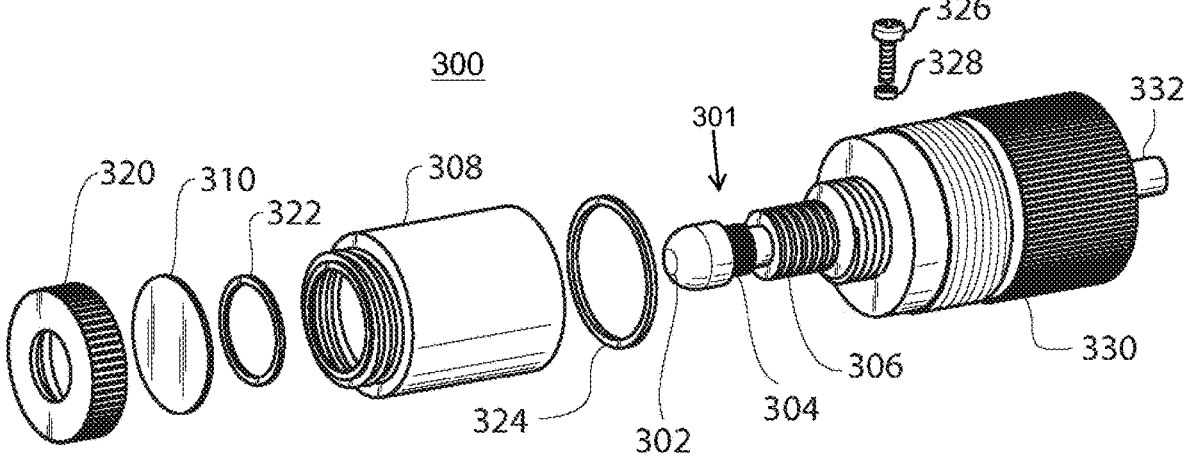
FIG. 3 is an exploded view of the thiosulfate sensor, according to an exemplary embodiment.

Using the system and method described above, a thiosulfate sensor in combination with an analyzer, further described below with reference to FIGS. 2 and 3, is configured for such monitoring in both potable and wastewater systems. Although a specific environment is shown as an example, the described sensor can be used in a variety of applications, such as being used to monitor thiosulfate concentrations in refinery where the excess level of thiosulfate is linked to corrosion of equipment and piping failure, being used in wastewater treatment to ensure no chlorine is being introduced into the environment, being used in combination with a microbial treatment to ensure that no chlorine will interfere with the microbial treatment, etc.

Referring now to FIG. 2, a thiosulfate monitoring system 200 is shown, according to an exemplary embodiment. The monitoring system 200 includes an analyzer 210, a flow cell assembly 220 and a thiosulfate sensor 300. Although an exemplary monitoring system is shown and described, one of ordinary skill in the art would understand that the system may be provided to include more, fewer, and/or a different configuration of component to implement the functionality described herein.

Analyzer 210 may be, for example, a Q46 monitor configured to operate in cooperating with sensor 300 to provide residual thiosulfate monitoring. Analyzers 210 may include an electrode excitation circuit, a control circuit, an electrode signal protection circuit and a signal processing circuit integrated into an electro-analyzer to implement the thiosulfate monitoring. Analyzer 210, in cooperation with sensor 300 is configured to detect thiosulfate in a range of 1-10 ppm, although with a potential range up to an including 50 ppm. Analyzer 210 includes a low voltage I/O wiring port 211, a relay wiring port 212, a digital communication wiring port 213, a power input port 214, such as a 12-24 VDC or 90-260 VAC port, a sensor communication port 215 and a user interface 216.

Analyzer 210 is in communication with sensor 300, positioned within flow cell assembly 220, through a sensor cable 217. Analyzer 210 is a readout device that receives an electrical signal from the sensor 300 over the sensor cable 217 and converts the electrical signal into the direct parts per million of the thiosulfate. Although a wired sensor cable 217 is shown and described, analyzer 210 may be configured to communicate through a wireless communication channel in an alternative embodiment.

Flow cell assembly 220 is configured to receive fluid from, for example, the utility supply network 114, through inlet line 221 including a flow valve 222 and an optional pressure regulator 223 for use with systems having variable pressure. In an exemplary embodiment, inlet line 221 may be implemented using ¼-inch piping. Inlet piping 221 may further include a sample tap 224 to divert fluid from the inlet line 221 for testing/validation of the monitoring system 220 using traditional residual thiosulfate detection tests in a laboratory environment using traditional instruments over a longer period of time.

Flow cell assembly 220 further includes a sample chamber 230 configured to receive sensor 300 and fluid from inlet line 221. Flow cell assembly 220 yet further includes a drain line 232 configured to drain tested fluid from the sample chamber 230. Drain line 232 may be implemented using ½-inch piping Although a particular thiosulfate monitoring system 200 is shown including a particular analyzer 210, flow cell assembly 220 and thiosulfate sensor 300 in a particular configuration, it should be understood that a variety of implementations may be provided to implement the functionality described herein.

Referring now to FIG. 3, a thiosulfate sensor 300 is shown in an exploded view, according to an exemplary embodiment. Sensor 300 provides a simple, convenient, rapid, accurate and precise measurement for real time monitoring for thiosulfate in potable water, wastewater, refinery, mining, textile and agricultural applications.

Thiosulfate ion (S2O3-2) sensor 300 includes an electrode assembly 301 that includes a sensing electrode 302, a reference electrode 304, and a counter electrode 306, an electrolyte chamber 308, a porous membrane 310, and a sensing element body 312.

The sensing electrode 302 is created using precious metal particles, such as Rhodium (—Rh), deposited electrochemically on to another precious metal surface such as gold (Au) or Platinum (Pt). The substrate may alternatively be any other non-metallic conductive surface such as glassy carbon, graphite or conductive polymeric materials. Rhodium nanoparticles were deposited electrochemically on a 0.25 inch diameter gold surface by submerging it in a mixture solution of 1.6 mM Rhodium (III) Chloride, 16 mM sodium citrate and 0.1M hypo chloric acid. The electrochemical deposition was performed at room temperature and in a standard 3 electrode configuration with gold as a working electrode, Ag/AgCl, as a reference and a Pt coil as counter electrode, carried out at a potential of –0.3V (vs. Ag/AgCl) for 5500 seconds. After that, the electrode 302 was taken out, washed with copious amount of distilled water and dried at room temperature air. In alternative embodiments, the electrode 302 materials may include iridium oxide nanoparticles, gold metal, gold nanoparticles, platinum metal, glassy carbon, etc. The deposited metal may be high surface area nanoparticles of the metal.

Although a particular sensing electrode 302 is described, the sensor may be generally formed by the deposition of particular catalytic particles on a conducting surface. Sensing electrode 302 is shown in a plastic support structure to support the electrode 302 relative to the reference electrode 304.

The reference electrode 304 is one or more Ag/AgCl coils. Although a particular number of coils are shown, the functionality may be implemented using a variety of configurations of the reference electrode 304. The reference electrode is configured to maintain the constant potential applied to the sensing electrode as described hereinbelow.

The counter electrode 306 is platinum wire. The counter electrode completes the circuit such that there is another cathodic reaction taking place on the counter electrode.

In operation, the sensing electrode 302, the reference electrode 304, and the counter electrode 306 are submerged within the electrolyte solution in electrolyte chamber 308.

The electrolyte chamber 308 is a chamber having 1.0 M KNO₃ employed as an exemplary electrolyte. More specifically, the electrolytes may include a specific salt at a specific concentration, such as potassium nitrate (KNO₃) having a concentration range of 0.5M to 2.0M, sodium perchlorate (NaClO₄) having a concentration range of 0.25M to 1.0M, pH 8.5 Tris HCI buffer (0.5-1.0M) as exemplary embodiments.

The porous membrane 310 may be a porous polyvinylidene difluoride (PVDF) that is a hydrophilic membrane that allows the fluid being monitored into the electrolyte chamber when the sensor 300 is deployed. In operation, when the fluid to be sensed enters the electrolyte chamber in the electrolyte, the fluid comes in contact with the sensing electrode and an applied potential is provided. In alternative embodiment, the porous membrane may be provided to include a poly ether sulfone, a hydrophilic PTFE membrane, a PETE polyester, or any hydrophilic membrane having a pore size 0.1 um to 2.0 um.

Analyzer 210 applies and controls the potential to oxidize the thiosulfate onto the sensing electrode 302. The anodic current generated at the sensing electrodes arises from the oxidation of thiosulfate ions. The magnitude of the signal obtained from the electrochemical oxidation of the thiosulfate ion is directly proportional to the thiosulfate present in the system. This signal can be used to quantify the concentration of thiosulfate in the sample. At the applied bias voltage, the thiosulfate oxidation adopts the following pathways: $2S_2O_3^{2-} \rightarrow S_4O_6^{2-} + 2e^-$.

The sensor 300 can be used for measuring thiosulfate and physically compensating changes of temperature of the solution to be detected and interference of other ions in the solution on the sensor without software calculation, so that the measurement precision and stability are improved and continuous measurement of the concentration of thiosulfate in water can be carried out.

Sensor 300 further includes a front nut 320, a front O-ring 322, a rear O-ring 324, a vent screw 326, a vent screw O-ring 328, and a sensor element body 330 to secure and seal the components of the sensor 300 to on another. The sensor element body 330 include a cable port 332 configured to attach to the sensor cable 217.

Referring now to FIG. 4, a chart 400 illustrates thiosulfate monitoring correlating current measured 410 in nA with a measured thiosulfate 420 in parts per million (ppm), according to an exemplary embodiment. Accordingly, sensor 300 provides a near linear current response 410 as a function of thiosulfate concentration 420.

This has been a description of exemplary embodiments, but it will be apparent to those of ordinary skill in the art that variations may be made in the details of these specific embodiments without departing from the scope and spirit of the present invention, and that such variations are intended to be encompassed by the following claims.

I claim:

1. A thiosulfate sensor, comprising:

an electrode assembly including a sensing electrode including electrochemically deposited metal, a counter electrode, and a reference electrode; and an electrolyte chamber including an electrolyte solution therein, the electrolyte chamber receiving the electrode assembly through a first opening to immerse the electrode assembly in the electrolyte and an electrolyte chamber porous membrane covering a second opening such that the sensing electrode, the counter electrode and the reference electrode are in contact with the electrolyte, wherein the porous membrane is configured to receive a flowing fluid therethrough to allow the detection of thiosulfate in the flowing fluid.

2. The sensor of claim 1, wherein the electrochemically deposited metal is at least one of rhodium, iridium oxide, gold, platinum, and glassy carbon.

3. The sensor of claim 2, wherein the deposited metal is high surface area nanoparticles of the metal.

4. The sensor of claim 1, wherein the electrolyte is at least one of potassium nitrate, sodium perchlorate and pH 8.5 Tris HCI buffer.

5. The sensor of claim 1, wherein the electrolyte chamber membrane is a hydrophilic membrane with pore size ranging from 0.1 um to 0.2 um.

6. The sensor of claim 5, wherein the electrolyte chamber membrane is at least one of polyvinylidene difluoride, poly ether sulfone, hydrophilic PTFE membrane, and PETE Polyester.

7. The sensor of claim 1, wherein the sensor assembly includes an analyzer connection configured to receive an applied bias potential to the electrode assembly.

8. A method for detecting residual thiosulfate in a flowing fluid in real time using a thiosulfate sensor, the method comprising:

positioning a thiosulfate sensor in a flow cell configured to receive fluid from the flowing fluid, the thiosulfate sensor including an electrode assembly including a sensing electrode including electrochemically deposited metal, a counter electrode, and a reference electrode; and an electrolyte chamber including an electrolyte therein, the electrolyte chamber receiving the electrode assembly through a first opening to immerse the electrode assembly in the electrolyte and an electrolyte chamber porous membrane covering a second opening such that the sensing electrode, the counter electrode and the reference electrode are in contact with the electrolyte, wherein the porous membrane is configured to receive a flowing fluid therethrough to allow the detection of thiosulfate in the flowing fluid; and applying a bias potential to the thiosulfate sensor in the flow cell to identify a thiosulfate concentration correlated to a measured current from the thiosulfate sensor.

9. The method of claim 8, wherein the electrochemically deposited metal for the sensing electrode is at least one of rhodium, iridium oxide, gold, platinum, and glassy carbon.

10. The method of claim 9, wherein the deposited metal is nanoparticles of the metal.

11. The method of claim 8, wherein the electrolyte in the electrolyte chamber is at least one of potassium nitrate, sodium perchlorate and pH 8.5 Tris HCI buffer.

12. The method of claim 8, wherein the electrolyte chamber membrane is a hydrophilic membrane with pore size ranging from 0.1 um to 0.2 um.

13. The sensor of claim 12, wherein the electrolyte chamber membrane is at least one of polyvinylidene difluoride, poly ether sulfone, hydrophilic PTFE membrane, and PETE Polyester.

14. The sensor of claim 8, wherein the sensor assembly includes an analyzer connection configured to receive the applied bias applied to the electrode assembly.

* * * * *